United States Patent [19]

Zupancic et al.

[11] Patent Number: 5,376,595
[45] Date of Patent: Dec. 27, 1994

[54] SILICON CARBOXIDE CERAMICS FROM SPIROSILOXANES

[75] Inventors: Joseph J. Zupancic, Bensenville; Roger Y. Leung, Schaumburg, both of Ill.

[73] Assignee: Allied-Signal Inc., Morris Township, Morris County, N.J.

[21] Appl. No.: 937,934

[22] Filed: Aug. 28, 1992

[51] Int. Cl.$^5$ .............................................. C03C 3/00
[52] U.S. Cl. ................................. 501/12; 528/27; 528/40; 528/55
[58] Field of Search ............... 528/27, 40; 501/12, 501/32, 55; 428/429, 447

[56] References Cited

U.S. PATENT DOCUMENTS

| | | | |
|---|---|---|---|
| Re. 29,760 | 9/1978 | Brown et al. | 525/41 |
| Re. 32,107 | 4/1986 | January | 501/12 |
| 3,197,432 | 7/1965 | Lamoreaux | 260/46.5 |
| 3,197,433 | 7/1965 | Lamoreaux | 260/46.5 |
| 3,271,362 | 9/1966 | Chalk et al. | 260/46.5 |
| 3,378,431 | 4/1968 | Smith et al. | 161/1 |
| 3,439,014 | 4/1969 | Patton et al. | 260/448.2 |
| 3,957,717 | 5/1976 | Harada et al. | 260/37 |
| 4,322,476 | 3/1982 | Molapi, Jr. | 428/412 |
| 4,599,394 | 7/1986 | Lucas | 525/15 |
| 4,618,591 | 10/1986 | Okamura et al. | 501/90 |
| 5,180,694 | 1/1993 | Renwald et al. | 501/12 |
| 5,231,059 | 7/1993 | Leung et al. | 501/12 |

FOREIGN PATENT DOCUMENTS

| | | |
|---|---|---|
| 0369091A1 | 5/1990 | European Pat. Off. . |
| 9213159 | 7/1993 | WIPO . |

OTHER PUBLICATIONS

Zachernyuk, A. B. et al. "Sunthesis and Structure of Polyspirocyclodimethylsiloxanes", Zhurnal Obshchei Khimii, vol. 57, No. 3, 1 Mar., 1987 pp. 562-567.

Primary Examiner—Karl Group
Assistant Examiner—A. Wright
Attorney, Agent, or Firm—Mary Jo Boldingh; Harold N. Wells; Roger H. Criss

[57] ABSTRACT

A carbon-containing black glass has the empirical formula $SiC_xO_y$ wherein x ranges from about 0.5 to about 2.0 and y ranges from about 0.5 to about 3.0 and is resistant to oxidation up to a temperature of about 1400° C. The black glass is synthesized by heating a spirosiloxane polymer in a non-oxidizing atmosphere up to a temperature in the range of from about 750° C. to about 1400° C. The polymers are synthesized by reacting the spirosiloxane oligomers:

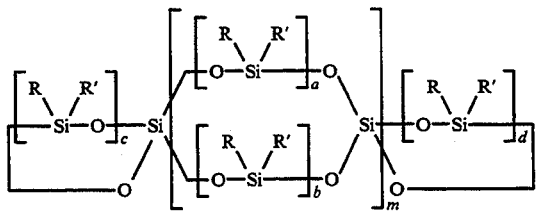

wherein a and b are integers from 0 to 20, preferably 1 to 5, c and d are integers from 2 to 20, preferably 2 to 6, m is an integer from 0 to 10, preferably 0 to 4, and wherein for each silicon atom in the oligomer having R and R' moieties, R is independently selected from the group consisting of alkyl groups from $C_1$ to $C_{20}$, preferably $C_1$ to $C_5$, and R' is independently selected from the group consisting of hydrogen, and alkenyl groups from $C_2$ to $C_{20}$, preferably from $C_2$ to $C_5$. The black glass may be used to make moldable complex shapes, filled monoliths, fibers, fiber-reinforced matrix composites, and coatings for substrates such as ceramics, polymers, and carbon-carbon composites.

40 Claims, No Drawings

OTHER PUBLICATIONS

U.S. application Ser. No. 002,049, filed Jan. 1987, Leung et al.

U.S. application Ser. No. 185,620, filed Apr. 1988, Leung.

U.S. application Ser. No. 523,620, filed May 1990, Leung et al.

U.S. application Ser. No. 685,303, filed Apr. 1991, Gonczy et al.

U.S. application Ser. No. 042,090, filed Apr. 1987, Leung et al.

U.S. application Ser. No. 689,590, filed Apr. 1991, Leung et al.

Elmer et al., *J. Amer. Ceramic Soc.*, 59, 206(1976) "Increase of Annealing Point of 96% $SiO_2$ Glass on Incorporation of Carbon".

Elmer, *Ceramic Bulletin*, 55, 999 (1976) "Electrical Properties of Carbon-Containing Reconstructed Silica Glass".

Shklover et al., *Adv. Organosilicon Chem.*, ed. M. G. Voronkov, 11 (1985) "Crystal and Molecular Structure of Organosilicon Compounds".

U.S. application Ser. No. 07/863,481, filed Apr. 1991, Leung et al.

Scott, *J. Amer. Chem. Soc.*, 68, 356 (1946) "Thermal Rearrangement of Branched-Chain Methylpolysiloxanes".

Kireev, *Adv. Polym. Chem.*, e.d. V. V. Korshak, 198 (1986) "Some Advances in the Chemistry of Organosilicon Polymers".

SILICON CARBOXIDE CERAMICS FROM SPIROSILOXANES

BACKGROUND OF THE INVENTION

Field of the Invention

This invention relates to ceramic materials which are oxidation-resistant, and temperature-resistant and to the process and compounds used in making these materials. In particular, the invention relates to silicon carboxide ceramics ("black glasses"), to the spirosiloxane oligomers and polymers which are precursors to the ceramics, and to the process for synthesizing the silicon carboxide ceramics and precursor compounds.

Ceramics have been tailored to improve properties such as durability, nonporosity, electrical conductivity or nonconductivity, thermal resistance, toughness, and ease of fabrication. One method of tailoring the properties of silica-containing ceramics has been to add carbon to make a silicon carboxide ceramic or "black glass." It has proven difficult, however, to prepare a black glass which has good stability at high temperature in an oxidizing atmosphere. It is one object of the present invention to provide a black glass having good stability at high temperatures in oxidizing atmospheres as well as having other desirable properties.

SUMMARY OF THE INVENTION

The present invention involves a novel black glass synthesized from novel spirosiloxane polymers. It also concerns novel spirosiloxane oligomers used to make the polymers as well as the methods of synthesizing the oligomers, polymers, and the black glass. The black glass may be used at high temperatures without converting from an amorphous to a crystalline material (i.e., the glass is devitrification resistant); it also contains oxidation-resistant carbon. It has potential use in the fabrication of moldable complex shapes, filled black glass monoliths, black glass fibers, fiber-reinforced black glass matrix composites, and coatings for substrates such as ceramics, polymeric substances, and carbon-carbon composites.

DETAILED DESCRIPTION OF THE INVENTION

Synthesis of Black

The carbon-containing black glass of this invention is a silicon carboxide or silicon oxycarbide which has the empirical formula $SiC_xO_y$ wherein x ranges from about 0.5 to about 2.0, preferably from 0.9 to 1.6, and y ranges from about 0.5 to about 3.0, preferably from 0.7 to 1.8. The glass is resistant to oxidation up to a temperature of about 1400° C. The black glass is synthesized by heating a spirosiloxane polymer in a non-oxidizing atmosphere up to a temperature in the range of from about 750° C. to about 1400° C. However, the process may be also carried out in an oxidizing atmosphere at a rate exceeding 5° C./min, preferably from about 50° C./min to about 1000° C./min, most preferably at a rate exceeding 100° C./min up to the same temperature range, and when the black glass is prepared in an oxidizing atmosphere, the empirical formula of the glass will be $SiC_xO_y$ wherein x is greater than zero to about 2, and y is greater than zero to about 2.2.

The black glass has an economical advantage in that the polymer may be formed at a low temperature and only the subsequent pyrolysis need be done at a high temperature. The char yield of the resulting black glass (the ratio of the weight of the pyrolyzed product to the weight of the product prior to pyrolysis) is superior (i.e., greater than 80%). The black glass is a very hard ceramic body that has applications as high temperature, oxidation-resistant, high strength composite matrices and castable ceramics. The glass may also be used to fabricate moldable complex shapes but with decreased dimensions due to thermal shrinkage.

Structure of Oligomers

The spirosiloxane polymer used to synthesize the black glass is itself synthesized by the hydrosilylation reaction of spirosiloxane oligomers. The spirosiloxane oligomer used to make the black glass has the structure:

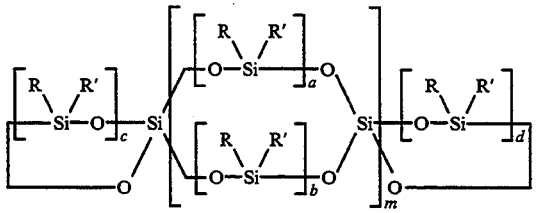

wherein a and b are integers from 0 to 20, preferably 1 to 5, c, and d are integers from 2 to 20, preferably 2 to 6, m is an integer from 0 to 10, preferably 0 to 4, and wherein for each silicon atom in the oligomer having R and R' moieties, R is independently selected from the group consisting of alkyl groups from $C_1$ to $C_{20}$, preferably $C_1$ to $C_5$, and R' is independently selected from the group consisting of hydrogen, and alkenyl groups from $C_2$ to $C_{20}$, preferably from $C_2$ to $C_5$, i.e., the R and R' moieties in any one ring system can be randomly distributed. Preferably, the vinyl carbon on the alkenyl group is directly bonded to the silicon atom.

Examples of the spirosiloxane oligomers are (1) wherein all R groups are methyl and all R' groups are hydrogen and a=1, b=1, c=2, d=2, and m=1; (2) wherein all R groups are methyl and all R' groups are vinyl and a=1, b=2, c=2, d=2, and m=1; and (3) wherein all R groups are methyl and the R' groups are either hydrogen or vinyl and are randomly distributed, and a=2, b=2, c=3, d=4, and m=1, e.g.,

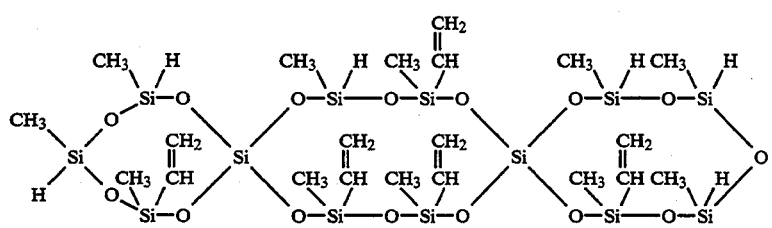

Synthesis of Spirosiloxane Polymer

The spirosiloxane polymer is synthesized by preparing a mixture of either (i) spirosiloxane oligomers wherein at least two R' groups are hydrogen and spirosiloxane oligomers wherein at least two R' groups are alkenyl or (ii) spirosiloxane oligomers wherein at least one R' is hydrogen and at least one R' is alkenyl and reacting the mixture in the presence of a hydrosilylation catalyst. A catalytically effective amount of a hydrosilylation catalyst is used to effect the polymerization, e.g., 0.3 to 200 ppm of a platinum complex, a rhodium complex, cobalt carbonyl, or manganese carbonyl. The molar ratios of the —SiH component to the —CH=CH$_2$ components may range from about 1:9 to about 9:1. The mixture is reacted at a temperature in the range of from about 20° C. to about 200° C. for a period of about 1 minute to about 5 days.

The polymerization occurs when a —SiH group on the oligomer reacts with a —CH=CH$_2$ group on another oligomer (an intermolecular reaction) to form a —Si—CH$_2$—CH$_2$— link (preferably, a —Si—CH$_2$CH$_2$—Si— link) wherein the alkenyl is bonded directly to the Si atom. Intramolecular hydrosilylation may occur when the same oligomer contains both hydrogen and alkenyl groups.

Synthesis of Oligomers

The spirosiloxane oligomers used to form the spirosiloxane polymers may be synthesized by either co-hydrolysis or an equilibrium reaction. The difficulty in the synthesis of a spirosiloxane lies in the choice of the solvent. A solvent system which favors the formation of the spiro-oligomer over a linear oligomer is preferred.

A process for synthesizing the spirosiloxane oligomer of claim 1 comprises the steps of (a) mixing a hydrocarbon solvent, an alcohol, and water; (b) adding a dichlorosilane and a second silicon compound to form the spirosiloxane oligomer; (c) separating the organic phase of the mixture from the aqueous phase; and (d) neutralizing and drying the organic phase and filtering to recover the spirosiloxane oligomer.

Examples of two novel oligomers are (1) hydromethylspirosiloxane ("HMSS"), wherein R is a methyl group and R' is hydrogen and , and (2) methylvinylspirosiloxane ("MVSS"), wherein R is a methyl group and R' is a vinyl group. In the synthesis of HMSS by cohydrolysis, a hydrocarbon solvent, an alcohol, and water are mixed, and cooled to a temperature in the range of about 0° to about 30° C., preferably about 0° to about 25° C. The solvent can be chosen from the C$_5$ to C$_{10}$ alkanes, e.g., hexane or heptane, and the alcohol can be chosen from the C$_1$ to C$_4$ alkyl alcohols, e.g., methanol or ethanol. A dichlorosilane (dichloromethylsilane) and a second silicon compound chosen from the group consisting of silicon tetrachloride and Si(OR")$_4$, wherein R" is a C$_1$ to C$_4$ alkyl group, e.g., ethoxy in tetraethoxysilane, are then added with stirring while maintaining the temperature. The silicon atom in the dichlorosilane is difunctional and the silicon in the second silicon compound is tetrafunctional. The ratio of the two components based upon silicon will range from a difunctional/tetrafunctional (D/T) ratio of 2:1 to a D/T ratio of 30:1, preferably within the range of a D/T ratio of 4:1 to 10:1. After the addition of the second silicon compound, the temperature is maintained for a period in the range of from about 0.5 to about 24 hours and the mixture then warmed to about room temperature. The organic phase of the mixture is then separated from the aqueous phase, and washed to neutralize the mixture, e.g., with sodium bicarbonate, dried, and filtered, and concentrated under vacuum to recover the hydromethylspirosiloxane.

The synthesis of MVSS by co-hydrolysis is carried out in the same manner except that the difunctional silane used is dichloromethylvinylsilane, and aromatic hydrocarbons such as toluene and benzene may be used in place of the C$_5$ to C$_{10}$ alkanes, with toluene as the preferred compound.

An alternative route to the synthesis of HMSS is by an equilibrium reaction between a tetraalkoxysilane and a cyclosiloxane. The process comprises (a) mixing a tetraalkoxysilane with a cyclosiloxane; (b) adding an alkane, an alcohol and an acid and stirring the mixture to form the spirosiloxane oligomer; (c) neutralizing the mixture; (d) separating the organic from the aqueous phase; and (e) washing and drying the organic phase and filtering to recover the spirosiloxane oligomer. The preferred tetraalkoxy compounds are tetramethoxysilane and tetraethoxysilane. The preferred cyclosiloxane is hydromethylcyclosiloxane which has the structure:

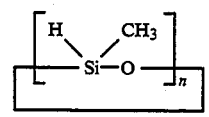

wherein n is an integer from 3 to 8. The molar ratio of the tetraalkoxy compound to the cyclosiloxane in the mixture will range from 1:10 to 1:2. To this mixture, a C$_5$ to C$_{10}$ alkane, a C$_1$ to C$_4$ alcohol, and an acid are added and the mixture stirred for a period of about 1 hour to 15 days. Preferred alkanes are pentane and hexane, the preferred alcohol is ethanol, and examples of acids are hydrochloric acid, sulfuric acid, and toluene sulfonic acid. The mixture is then neutralized, e.g., with sodium bicarbonate, and the organic phase washed, dried, and filtered to recover the HMSS.

MVSS may be synthesized by an equilibrium reaction in the same manner except that a vinyl-containing cyclosiloxane such as methylvinylcyclosiloxane is used in place of hydromethylcyclosiloxane; methylvinylcyclosiloxane has the structure:

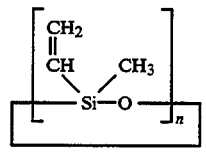

wherein n is equal to an integer from 3 to 8.

Applications

The spirosiloxane oligomer mixture can be used to form a black glass coating on surfaces such as ceramic, carbon-carbon composite, metals, and polymer composites. The coating may be prepared by coating a surface with a hydrosilylation catalyst and a mixture of either (i) spirosiloxane oligomers wherein at least two R' groups are hydrogen and spirosiloxane oligomers wherein at least two R' groups are alkenyl or (ii) spirosiloxane oligomers wherein at least one R' is hydrogen and at least one R' is alkenyl, reacting to form a spirosiloxane polymer on the surface, and heating the polymer-coated surface as discussed above to form the black glass coating. Alternatively, the coating may be prepared by coating a surface with the preformed spirosiloxane polymer and then heating the polymer-coated surface to form the coating.

The spirosiloxane oligomer mixture can also be used to form a matrix for a composite, e.g., a black glass matrix with a filler. The composite may be prepared by mixing the spirosiloxane polymer with a filler and heating the mixture to form the composite. Examples of fillers are cubic or hexagonal silicon carbide, silicon nitride, silica, alumina, hafnia, titania, and zirconia to strengthen the resulting composite. The fillers may be in the form of powders, whiskers, chopped fibers, or continuous fibers and can be mixed into the monomer using conventional means. The filled product spirosiloxane polymer produced by the process of this invention shows not only increased strength by also exhibits controlled shrinkage upon the pyrolysis step.

Densification of Black Glass

Also considered as within the scope of this invention is a process involving further impregnating the black glass product of this invention with more of the spirosiloxane oligomer mixture. The best results are achieved by pressure or vacuum impregnation. The impregnated product is again pyrolyzed to afford a black glass product with fewer cracks and voids and with greater density. Impregnation may be done repeatedly to further increase the density of the black glass product.

Synthesis of Methylvinylspirosiloxane (MVSS)

EXAMPLE 1

MVSS was synthesized by a co-hydrolysis reaction by first charging 190.0 mL (10,555 moles) of water, 302.0 mL (7.456 moles) of methanol, and 468.0 mL (4,394 moles) toluene into a 2 liter three-neck round bottom flask equipped with magnetic stirrer, thermometer, condenser, nitrogen purge, addition funnel and sodium bicarbonate trap. The reaction mixture was cooled to 0±2° C., and then a mixture of 200.0 mL (1.531 moles) of dichloromethylvinylsilane and 14.6 mL (0.127 moles) of silicon tetrachloride was added over a 3 hour period with stirring. The reaction was maintained at 0±2° C. during this addition and for 1 hour afterwards and then warmed to room temperature. The reaction mixture was transferred to a separatory funnel and the organic phase washed with 500 mL of 5% sodium bicarbonate solution and 500 mL of water, dried over sodium sulfate, filtered and concentrated under vacuum, yielding 133.7 g (95.81% yield) of MVSS.

The MVSS possessed a viscosity of 5.6 cps. Infrared spectroscopy and proton NMR indicated that no Si-OH moiety was present. Gel permeation chromatography (GPC) indicated that the number average molecular weight, Mn, was 550, the weight average molecular weight, Mw, was 600, and the dispersity (Mw/Mn) was 1.1. The MVSS spiro oligomer consisted of both difunctional silicone units (D) and tetrafunctional silicone units (T). The D/T ratio was 12.

EXAMPLE 2

MVSS was synthesized by the procedure of Example 1 except that the amount of silicon tetrachloride added was 29.2 mL (0.255 moles) and after filtering, the reaction mixture was filtered a second time through Celite. The synthesis yielded 133.3 g (90.53% yield) of MVSS with a viscosity of 12.9 cps. Infrared and NMR indicated that there was no Si-OH moiety present. GPC analysis showed Mn=650, Mw=800, and a dispersity of 1.2. The D/T ratio was 6.

EXAMPLE 3

MVSS was synthesized by the procedure of Example 1 except that the amount of silicon tetrachloride added was 43.8 mL (0.382 moles) which was added over a 4.75 hour period, and, after filtering, the reaction mixture was filtered a second time through Celite. The synthesis yielded 85.3 g (55.08% yield) of MVSS with a viscosity of 22.2 cps. Infrared and NMR indicated that there was no Si-OH moiety present. GPC analysis showed Mn=700, Mw=1000, and a dispersity of 1.4. The D/T ratio was 4.

EXAMPLE 4

MVSS was synthesized by an equilibrium reaction by charging 2.50 grams (0.0120 moles) of tetraethoxysilane and 35.50 g (0.413 moles of the —Si(CH=CH$_2$)(CH$_3$)—O— repeat unit) of methylvinylcyclosiloxane (having 84.53% n=4, 14.20% n=5, 0.59% n=6) into a 250 mL round bottom flask equipped with stopper and stirring bar. 100 mL (0.868 moles) of pentane and 50 mL (0.852 moles) of absolute ethanol were added to the reaction mixture and the mixture was stirred. 2.00 mL (0.024 moles) of concentrated hydrochloric acid was then added to the reaction mixture and the stirring was increased for improved mixing. The mixture was stirred for 13 days at room temperature and was then neutralized by adding sodium bicarbonate. The mixture was transferred to separatory funnel. The organic phase was washed twice with 250 mL of deionized water, dried over magnesium sulfate, filtered and concentrated under vacuum to yield 32.78 grams (90.50% yield) of a clear liquid (MVSS). The MVSS was found to have a viscosity of 7.7 cps and IR and NMR analysis indicated no Si-OH moiety present. GPC analysis showed Mn=580, Mw=780, and a dispersity of 1.4. The D/T ratio was 34.

Synthesis of Hydromethylspirosiloxane (HMSS)

EXAMPLE 5

HMSS was synthesized by a co-hydrolysis reaction by first charging 95.6 mL (5.311 moles) of water, 400.0 mL (9.875 moles) of methanol, and 703.6 mL (5.380 moles) of hexane into a 2 liter three-neck round bottom flask equipped with magnetic stirrer, thermometer addition funnel, nitrogen purge, sodium bicarbonate trap and condenser. The reaction mixture was cooled to 20° C. and then a mixture of 159.3 mL (1.530 moles) of dichloromethylsilane and 14.6 mL (0.127 moles) of silicon tetrachloride was added to the reaction medium over a 4 hour period while maintaining a reaction temperature of 20±2° C. The reaction was maintained at 20±2° C. for 1 hour with stirring and then transferred to a separatory funnel. The organic phase was washed with 500 mL of 5% sodium bicarbonate solution and then with 500 mL of water, dried over sodium sulfate, filtered and then concentrated under vacuum, yielding 89.0 g (89.33% yield) of HMSS. The viscosity of the HMSS was 6.0 cps and IR and proton NMR analysis indicated that there was no Si-OH moiety present. GPC analysis showed Mn=650, Mw=1500, and a dispersity of 2.3. The D/T ratio was 12.

EXAMPLE 6

HMSS was synthesized by a co-hydrolysis reaction by first charging 191.2 mL (10.622 moles) of water, 800.0 mL (19,750 moles) of methanol, and 1407.0 mL (10.759 moles) of hexane into a 5 liter three-neck round bottom flask equipped with magnetic stirrer, thermometer addition funnel, nitrogen purge, sodium bicarbonate trap and condenser. The reaction mixture was cooled to 10±2° C. and then a mixture of 318.6 mL (3.060 moles) of dichloromethylsilane and 43.8 mL (0.382 moles) of silicon tetrachloride was added to the reaction medium over a 4 hour period while maintaining a reaction temperature of 10±2° C. The reaction was maintained at 10±2° C. for 1 hour with stirring, warmed to ambient temperature and then transferred to a separatory funnel. The organic phase was washed twice with 500 mL of 5% sodium bicarbonate solution and then with 500 mL of water, dried over sodium sulfate, filtered, and filtered a second time through Celite, and then concentrated under vacuum, yielding 136.2 g (65.81% yield) of HMSS with a viscosity of 7.2 cps. IR and NMR analysis indicated that no Si-OH moiety was present and GPC analysis showed Mn=710, Mw=1500, and a dispersity of 2.1. The D/T ratio was 8.

EXAMPLE 7

HMSS was synthesized by an equilibrium reaction by charging 2.21 grams (0.0106 moles) of tetraethoxysilane and 24.50 g (0.4083 moles of the —Si(H)(CH$_3$)—O— repeat unit) of hydromethylcyclosiloxane (having 14.47% n=4, 40.07% n=5, 21.25% n=6, 8.07% n=7, 2.91% n=8, 1.72% n=9, 1.20% n=10, 0.94% n=11, and 0.79% n=12) into a 300 mL round bottom flask equipped with stopper and stirring bar. 100 mL (0.868 moles) of pentane and 50 mL (0.852 moles) of absolute ethanol were added to the reaction mixture and the mixture was stirred. 2.00 mL (0.024 moles) of concentrated hydrochloric acid was added to the mixture and the stirring was increased for improved mixing, the mixture was stirred for 13 days at room temperature. The mixture was neutralized via addition of sodium bicarbonate. The mixture was transferred to separatory funnel with pentane and water. The organic phase was washed twice with 250 mL of deionized water, dried over magnesium sulfate, filtered and concentrated under vacuum to yield 22.28 grams (88.63% yield) of a clear liquid (HMSS). The HMSS was found to have a viscosity of 10.9 cps and IR and NMR analysis indicated that no Si-OH moiety was present. GPC analysis showed Mn=1500, Mw=17000, and a dispersity of 12.0. The D/T ratio was 38.5.

Synthesis of a Silicon Carboxide Ceramic (or "Black Glass")

EXAMPLE 8

Black glass was synthesized by mixing 13.94 g of MVSS prepared in Example 1, 9.74 g of HMSS prepared in Example 5, and 0.15 g of a platinum/methylvinylcyclosiloxane complex containing 0.5% Pt in toluene. The platinum concentration in the reaction mixture was 32 ppm. The mixture was held at 25° for 4 days, at 50° C. for 2 hours, and finally at 100° C. for 16 hours. The product was a clear solid polymer.

The polymer was heat-treated in flowing nitrogen to convert it to a ceramic by heating it to 850° C. over an 8 hour period, maintaining the temperature at 850° C. for 30 minutes, and then cooling to 50° C. over a 6 hour period. A black-colored ceramic was obtained with char yield of 80.2%. Elemental analysis showed that the ceramic material contained 21.9 wt % carbon and 43.6 wt % silicon. As the amount of hydrogen and nitrogen is less than 0.5%, the oxygen content was calculated by difference to be 34.5 wt %. The empirical formula was therefore determined to be $SiC_{1.17}O_{1.38}$.

EXAMPLE 9

Black glass was synthesized by the procedure described in Example 8 except that 13.49 g MVSS prepared in Example 2 was used. A black ceramic was obtained with char yield of 81.2%. Elemental analysis showed that the ceramic contained 21.6 wt % carbon and 44.6 wt % silicon. The oxygen content was calculated to be 33.8 wt % by difference. The empirical formula was therefore determined to be $SiC_{1.13}O_{1.32}$.

EXAMPLE 10

Black glass was synthesized by the procedure described in Example 8 except that 13.49 g of MVSS prepared in Example 3 was used. A black ceramic was obtained with char yield of 85.7%. Elemental analysis showed that the ceramic contained 20.3 wt % carbon and 44.4 wt % silicon. The oxygen content was calculated to be 35.3 wt % by difference. The empirical formula was therefore determined to be $SiC_{1.07}O_{1.39}$.

EXAMPLE 11

Black glass was synthesized by the procedure described in Example 8 except that 13.49 g of MVSS prepared in Example 1 and 9.74 g of HMSS prepared in Example 6 were used. A black ceramic was obtained with char yield of 84.9%. Elemental analysis showed that the ceramic contained 21.0 wt % carbon and 44.4 wt % silicon. The oxygen content was calculated to be 34.6 wt % by difference. The empirical formula was therefore determined to be $SiC_{1.10}O_{1.36}$.

EXAMPLE 12

Black glass was synthesized by the procedure described in Example 8 except that 13.49 g of MVSS prepared in Example 2 and 9.74 g of HMSS prepared in Example 6 were used. A black ceramic was obtained with char yield of 5.7%. Elemental analysis showed that the ceramic contained 20.2 wt % carbon and 44.4 wt % silicon. The oxygen content was calculated to be 35.4 wt % by difference. The empirical formula was therefore determined to be $SiC_{1.06}O_{1.40}$.

EXAMPLE 13

Black glass was synthesized by the procedure described in Example 8 except that 13.49 g of MVSS prepared in Example 3 and 9.74 g of HMSS prepared in Example 6 were used. A black ceramic was obtained with char yield of 86.1%. Elemental analysis showed that the ceramic contained 20.1 wt % carbon and 44.5 wt % silicon. The oxygen content was calculated to be 35.4 wt % by difference. The empirical formula was therefore determined to be $SiC_{1.05}O_{1.39}$.

EXAMPLE 14

Black glass was synthesized by the procedure described in Example 8 except that 13.49 g of MVSS prepared in Example 4 and 9.74 g of HMSS prepared in Example 7 were used. A black ceramic was obtained with char yield of 82.5%. Elemental analysis showed that the ceramic contained 25 wt % carbon. The weight percents of silicon and oxygen were estimated to be about 44% and 31% respectively. The empirical formula was therefore determined to be $SiC_{1.33}O_{1.23}$.

EXAMPLE 15

The pyrolyzed product (black glass) from Example 14 was analyzed by solid state magic angle spinning $^{29}Si$ nuclear magnetic resonance spectroscopy. The spectrum was acquired at 59.502 MHz on a Chemagnetics CMX300 NMR spectrometer. Data was obtained by the single pulse technique without decoupling. Recycle time was 600 seconds with 284 scans, The sodium salt of propanesulfonic acid was used to calibrate the chemical shift (1.18 ppm). The NMR peaks were deconvoluted using NMRI computer software and a Gaussian lineshape function was employed to resolve the peaks. The characteristics of the deconvoluted peaks are listed in Table I.

TABLE I

| Chemical Shift (ppm) | Assignment | Percentage |
| --- | --- | --- |
| −115 | Si—O$_4$ | 10.3% |
| −72 | C—Si—O$_3$ | 42.7% |
| −27 | C$_2$—Si—O$_2$ | 31.2% |
| −2 | C$_3$—Si—O or C$_4$—Si | 15.8% |

The NMR data show different silicon configurations consisting of different combinations of bonded oxygen and carbon atoms,

EXAMPLE 16

The solid state $^{29}Si$ NMR spectrum of the black glass from Example 9 was obtained under the conditions described in Example 15. The chemical shifts and percentages are listed in the Table II.

TABLE II

| Chemical Shift (ppm) | Assignment | Percentage |
| --- | --- | --- |
| −112 | Si—O$_4$ | 12.8% |
| −72 | C—Si—O$_3$ | 36.5% |
| −27 | C$_2$—Si—O$_2$ | 31.3% |
| −4 | C$_3$—Si—O or C$_4$—Si | 19.4% |

EXAMPLE 17

Black glass chunks obtained from Examples 9 to 13 were heated in stagnant air at 900° C. for 19 hours. The average weight loss measured was between 2% and 3%. The weight loss can be attributed to the effect of continuing pyrolysis due to the temperature increase to 900° C. from the previous 850° C. processing temperature. The weight loss and the final carbon content after the 900° C./19h/air treatment are listed in Table III.

TABLE III

| Black Glass Example No. | Weight Loss | Carbon wt % (900° C./19 h/air) | Initial Carbon wt % |
| --- | --- | --- | --- |
| 9 | 2.9% | 22.7% | 21.6% |
| 10 | 2.3% | 22.1% | 20.3% |
| 11 | 2.4% | 23.6% | 21.0% |
| 12 | 2.5% | 22.6% | 20.2% |
| 13 | 2.2% | 21.6% | 20.1% |

These data show that the carbon content of the black glass after heating in air for 19 hours at approximately 900° C. is at the same level (within experimental uncertainty) as carbon content of the samples treated at 850° C. despite the 2% weight loss. This demonstrates that the carbon in the black glass is resistant to oxidation at high temperatures.

We claim:
1. A spirosiloxane oligomer having the formula:

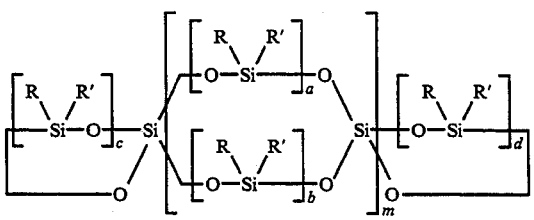

wherein a and b are integers from 0 to 20, c and d are integers from 2 to 20, m is an integer from 0 to 10, and wherein for each silicon atom in the oligomer having R and R' moieties R is independently selected from the group consisting of alkyl groups from $C_1$ to $C_{20}$, and R' is independently selected from the group consisting of hydrogen and alkenyl groups from $C_2$ to $C_{20}$.

2. The spirosiloxane oligomer of claim 1 wherein all R groups are methyl and all R' groups are hydrogen.

3. The spirosiloxane oligomer of claim 1 wherein all R groups are methyl and all R' groups are vinyl.

4. The spirosiloxane oligomer of claim 1 wherein a and b are integers from 1 to 5, c and d are integers from 2 to 6, m is an integer from 0 to 4, and R is independently selected from the group consisting of alkyl groups from $C_1$ to $C_5$ and R' is independently selected from the group consisting of hydrogen and alkenyl groups from $C_2$ to $C_5$.

5. The spirosiloxane oligomer of claim 4 wherein all R groups are methyl and all R' groups are hydrogen.

6. The spirosiloxane oligomer of claim 4 wherein all R groups are methyl and all R' groups are vinyl.

7. A spirosiloxane polymer prepared by the process comprising:
(a) preparing a mixture of spirosiloxane oligomers wherein the mixture comprises spirosiloxane oligomers of claim 1 wherein at least two R' groups are hydrogen and spirosiloxane oligomers of claim 1 wherein at least two R' groups are alkenyl; and
(b) reacting the mixture in the presence of a hydrosilylation catalyst to form the spirosiloxane polymer.

8. A spirosiloxane polymer prepared by the process comprising:
(a) preparing a mixture of spirosiloxane oligomers wherein the mixture comprises spirosiloxane oligomers of claim 1 wherein at least one R' is hydrogen and at least one R' is alkenyl; and
(b) reacting the mixture in the presence of a hydrosilylation catalyst to form the spirosiloxane polymer.

9. A spirosiloxane polymer prepared by the process comprising the steps of:
(a) mixing the spirosiloxane oligomer of claim 2 and the spirosiloxane oligomer of claim 3; and
(b) reacting the mixture in the presence of a hydrosilylation catalyst to form the spirosiloxane polymer.

10. A carbon-containing black glass having resistance to oxidation below 1400° C. and having the empirical formula $SiC_xO_y$ wherein x ranges from about 0.5 to about 2, and y ranges from about 0.5 to about 3.0, and wherein grater than 87 percent of the silicon atoms have at least one bond to a carbon atom, said black which is prepared by the process comprising heating a spirosiloxane polymer in a non-oxidizing atmosphere up to a temperature in the range of from about 750° C. to about 1400° C., said spirosiloxane polymer which is prepared by the process comprising:
(a) preparing a mixture of spirosiloxane oligomers wherein the mixture comprises spirosiloxane oligomers of claim 1 wherein at least two R' groups are hydrogen and spirosiloxane oligomers of claim 1 wherein at least two R' groups are alkenyl; and
(b) reacting the mixture in the presence of a hydrosilylation catalyst to form the spirosiloxane polymer.

11. A carbon-containing black glass having resistance to oxidation below 1400° C. and having the empirical formula $SiC_xO_y$ wherein x is greater than zero to about 2, and y is greater than zero to about 2.2, and wherein greater than 87 percent of the silicon atoms have at least one bond to a carbon atom, said black glass which is prepared by the process comprising heating a spirosiloxane polymer in an oxidizing atmosphere up to a temperature in the range of from about 750° C. to about 1400° C., said spirosiloxane polymer which is prepared by the process comprising:
(a) preparing a mixture of spirosiloxane oligomers wherein the mixture comprises spirosiloxane oligomers of claim 1 wherein at least two R' groups are hydrogen and spirosiloxane oligomers of claim 1 wherein at least two R' groups are alkenyl; and
(b) reacting the mixture in the presence of a hydrosilylation catalyst to form the spirosiloxane polymer.

12. The black glass of claim 10 wherein x ranges from about 0.9 to about 1.6, and y ranges from about 0.7 to about 1.8.

13. A carbon-containing black glass having resistance to oxidation below 1400° C. and having the empirical formula $SiC_xO_y$ wherein x ranges from about 0.5 to about 2, and y ranges from about 0.5 to about 3.0, and wherein greater than 87 percent of the silicon atoms have at least one bond to a carbon atom, said black glass which is prepared by the process comprising heating a spirosiloxane polymer in a non-oxidizing atmosphere up to a temperature in the range of from about 750° C. to about 1400° C., said spirosiloxane polymer which is prepared by the process comprising:
(a) mixing the spirosiloxane oligomer of claim 2 and the spirosiloxane oligomer of claim 3; and
(b) reacting the mixture in the presence of a hydrosilylation catalyst to form the spirosiloxane polymer.

14. A carbon-containing black glass having resistance to oxidation below 1400° C. and having the empirical formula $SiC_xO_y$ wherein x is greater than zero to about 2, and y is greater than zero to about 2.2, and wherein greater than 87 percent of the silicon atoms have at least one bond to a carbon atom said black glass which is prepared by the process comprising heating a spirosiloxane polymer in an oxidizing atmosphere up to a temperature in the range of from about 750° C. to about 1400° C., said spirosiloxane polymer which is prepared by the process comprising:
(a) mixing the spirosiloxane oligomer of claim 2 and the spirosiloxane oligomer of claim 3; and
(b) reacting the mixture in the presence of a hydosilylation catalyst to form the spirosiloxane polymer.

15. A process to produce to produce a black glass having greater than 87 percent of its silicon atoms with at least one bond to a carbon atom, said process which comprises heating a spirosiloxane polymer up to a temperature in the range of from about 750° C. to about 1400° C. in an oxidizing or a non-oxidizing atmosphere, said spirosiloxane polymer which is prepared by the process comprising:
(a) preparing a mixture of spirosiloxane oligomers wherein the mixture comprises spirosiloxane oligomers of claim 1 wherein at least two R' groups are hydrogen and spirosiloxane oligomers of claim 1 wherein at least two R' groups are alkenyl; and
(b) reacting the mixture in the presence of a hydrosilylation catalyst to form the spirosiloxane polymer.

16. The process of claim 15 wherein the black glass is prepared by heating the polymer in a non-oxidizing atmosphere.

17. A black glass coating having greater than 87 percent of its silicon atoms with at least one bond to a carbon atom, said coating which is prepared by the process comprising the steps of:
(a) coating a surface with the oligomeric mixture of claim 7(a) and a hydrosilylation catalyst;
(b) reacting the mixture to form a spirosiloxane polymer on the surface; and
(c) heating the polymer-coated surface up to a temperature in the range of from about 750° C. to about 1400° C. in an oxidizing or a non-oxidizing atmosphere to form the coating.

18. A black glass coating having greater than 87 percent of its silicon atoms with at least one bond to a carbon atom, said coating which is prepared by the process comprising the steps of:
(a) coating a surface with the spirosiloxane polymer of claim 7; and
(b) heating the polymer-coated surface up to a temperature in the range of from about 750° C. to about 1400° C. in an oxidizing or a non-oxidizing atmosphere to form the coating.

19. A filled black glass composite having greater than 87 percent of its silicon atoms with at least one bond to a carbon atom, said composite which is prepared by the process comprising the steps of:
(a) mixing the polymer of claim 7 with a filler chosen from the group consisting of alumina, hafnia, titania, and zirconia, or mixtures thereof, said filler which may be in the form of a powder or whiskers; and
(b) heating the mixture up to a temperature in the range of from about 750° C. to about 1400° C. in an oxidizing or a non-oxidizing atmosphere to form the composite.

20. A filled black glass composite having greater than 87 percent of its silicon atoms with at least one bond to a carbon atom, said composite which is prepared by the process comprising the steps of
(a) mixing the polymer of claim 7 with a filler chosen from the group consisting of cubic silicon carbide, hexagonal silicon carbide, silicon nitride, and silica, or mixtures thereof, said filler which may be in the form of a powder, whiskers, chopped fibers, continuous fibers; and
(b) heating the mixture up to a temperature in the range of from about 750° C. to about 1400° C. in an oxidizing or a non-oxidizing atmosphere to form the composite.

21. The composite of claim 20 wherein the filler is a continuous fiber.

22. A process for synthesizing the spirosiloxane oligomer of claim 1 comprising the steps of:
(a) mixing a hydrocarbon solvent chosen from the group consisting of the $C_5$ to $C_{10}$ alkanes, an alcohol chosen from the group consisting of the $C_1$ to $C_4$ alkyl alcohols, and water;
(b) adding a dichlorosilane having the substitutions R and R' wherein R is selected from the group consisting of alkyl groups from $C_1$ to $C_{20}$, and R' is hydrogen, and a second silicon compound chosen from the group consisting of silicon tetrachloride and $Si(OR'')_4$, wherein $R''$ is a $C_1$ to $C_4$ alkyl group, to the mixture to form the spirosiloxane oligomer;
(c) separating the organic phase of the mixture from the aqueous phane; and
(d) neutralizing and drying the organic phase and filtering to recover the spirosiloxane oligomer.

23. The process of claim 22 wherein the second silicon compound is silicon tetrachloride.

24. The process of claim 22 wherein the second silicon compound is tetraethoxysilane.

25. The process of claim 22 wherein the solvent is hexane and the alcohol is methanol.

26. A spirosiloxane oligomer formed by the process comprising the steps of:
(a) mixing a hydrocarbon solvent chosen from the group consisting of the $C_5$ to $C_{10}$ alkanes, an alcohol chosen from the group consisting of the $C_1$ to $C_4$ alkyl alcohols, and water;
(b) adding a dichlorosilane having the substitutions R and R' wherein R is selected from the group consisting of alkyl groups from $C_1$ to $C_{20}$, and R' is hydrogen, and a second silicon compound chosen from the group consisting of silicon tetrachloride and $Si(OR'')_4$, wherein $R''$ is $C_1$ to $C_4$ alkyl group, to the mixture to form the spirosiloxane oligomers;
(c) separating the organic phase of the mixture from the aqueous phase; and
(d) neutralizing and drying the organic phase and filtering to recover the spirosiloxane oligomer.

27. The process of claim 22 wherein the dichlorosilane substitution R is selected from the group consisting of alkyl groups from $C_1$ to $C_5$.

28. The process of claim 27 wherein the dichlorosilane is dichloromethylsilane.

29. A process for synthesizing the spirosiloxane oligomer of claim 1 comprising the steps of:
(a) mixing a hydrocarbon solvent chosen from the group consisting of the aromatic hydrocarbons and the $C_5$ to $C_{10}$ alkanes, an alcohol chosen from the group consisting of the $C_1$ to $C_4$ alkyl alcohols, and water;
(b) adding a dichlorosilane having the substitutions R and R' wherein R is selected from the group consisting of alkyl groups from $C_1$ to $C_{20}$, and R' is selected from the group consisting of alkenyl groups from $C_2$ to $C_{20}$, and a second silicon compound chosen from the group consisting of silicon tetrachloride and $Si(OR'')_4$, wherein $R''$ is a $C_1$ to $C_4$ alkyl group, to the mixture to form the spirosiloxane oligomer;
(c) separating the organic phase of the mixture from the aqueous phase; and
(d) neutralizing and drying the organic phase and filtering to recover the spirosiloxane oligomer.

30. The process of claim 29 wherein the dichlorosilane substitution R selected from the group consisting of alkyl groups from $C_1$ to $C_5$, and the dichlorosilane substitution R' is selected from the group consisting of alkenyl groups from $C_2$ to $C_5$.

31. The process of claim 29 wherein the dichlorosilane is dichloromethylvinylsilane.

32. The process claim 29 wherein the second silicon compound is silicon tetrachloride.

33. The process of claim 29 wherein the solvent is toluene and the alcohol is methanol.

34. A spirosiloxane oligomer formed by the process comprising the steps of:
(a) mixing a hydrocarbon solvent chosen from the group consisting of the aromatic hydrocarbons and the $C_5$ to $C_{10}$ alkanes, an alcohol chosen from the group consisting of the $C_1$ to $C_4$ alkyl alcohols, and water;
(b) adding a dichlorosilane having the substitutions R and R' wherein R is selected from the group consisting of alkyl groups from $C_1$ to $C_{20}$, and R' is selected from the group consisting of alkenyl groups from $C_2$ to $C_{20}$, and a second silicon compound chosen from the group consisting of silicon tetrachloride and $Si(OR'')_4$, wherein $R''$ is a $C_1$ to $C_4$ alkyl group, to the mixture to form the spirosiloxane oligomer;
(c) separating the organic phase of the mixture from the aqueous phase; and
(d) neutralizing and drying the organic phase and filtering to recover the spirosiloxane oligomer.

35. A process for synthesizing the spirosiloxane oligomer of claim 1 comprising the steps of:
(a) mixing a $Si(OR'')_4$, wherein $R''$ is a $C_1$ to $C_4$ alkyl group, with a cyclosiloxane having the substitutions R and R' wherein R is selected from the group consisting of alkyl groups from $C_1$ to $C_{20}$, and R' is selected from the group consisting of alkenyl groups from $C_2$ to $C_{20}$;
(b) adding a $C_5$ to $C_{10}$ alkane, a $C_1$ to $C_4$ alcohol and an acid and stirring the mixture to form the spirosiloxane oligomer;
(c) neutralizing the mixture;
(d) separating the organic from the aqueous phase; and
(e) washing and drying the organic phase and filtering to recover the spirosiloxane oligomer.

36. The process of claim 35 wherein the tetraalkoxysilane is tetraethoxysilane and the cyclosiloxane is a hydromethylcyclosiloxane.

37. The process of claim 35 wherein the tetraalkoxy compound is tetraethoxysilane and the cyclosiloxane is methylvinylcyclosiloxane.

38. A spirosiloxane oligomer formed by the process comprising the steps of:
(a) mixing a $Si(OR'')_4$, wherein $R''$ is a $C_1$ to $C_4$ alkyl group, with a cyclosiloxane having the substitutions R and R' wherein R is selected from the group consisting of alkyl groups from $C_1$ to $C_{20}$, and R' is selected from the group consisting of alkenyl groups from $C_2$ to $C_{20}$;
(b) adding a $C_5$ to $C_{10}$ alkane, a $C_1$ to $C_4$ alcohol and an acid and stirring the mixture to form the spirosiloxane oligomer;
(c) neutralizing the mixture;
(d) separating the organic from the aqueous phase; and (e) washing and drying the organic phase and filtering to recover the spirosiloxane oligomer.

39. A carbon-containing black glass having resistance to oxidation below 1400° C. and having the empirical formula $SiC_xO_y$ wherein x ranges from about 0.5 to about 2, and y ranges from about 0.5 to about 3.0, having greater than 83 percent of its silicon atoms with at least one bond to a carbon atom, said black glass which is prepared by the process comprising heating a spirosiloxane polymer in a non-oxidizing atmosphere up to a temperature in the range of from about 750° C. about 1400° C., said spirosiloxane polymer which is prepared by the process comprising:

(a) preparing a mixture of spirosiloxane oligomers wherein the mixture comprises spirosiloxane oligomers of claim 1 wherein at least one R' is hydrogen and at least one R' is alkenyl; and (b) reacting the mixture in the presence of a hydrosilylation catalyst to form the spirosiloxane polymer.

40. A carbon-containing black glass having resistance to oxidation below 1400° C. and having the empirical formula $SiC_xO_y$ wherein x is greater than zero to about 2, and y is greater than zero to about 2.2, and wherein greater than 87 percent of the silicon atoms have at least one bond to a carbon atom, said black glass which is prepared by the process comprising heating a spirosiloxane polymer in an oxidizing atmosphere up to a temperature in the range of from about 750° C. to about 1400° C., said spirosiloxane polymer which is prepared by the process comprising:

(a) preparing a mixture of spirosiloxane oligomers wherein the mixture comprises spirosiloxane oligomers of claim 1 wherein at least one R' is hydrogen and at least one R' is alkenyl; and (b) reacting the mixture in the presence of a hydrosilylation catalyst to form the spirosiloxane polymer.

* * * * *